(12) United States Patent
Dirks et al.

(10) Patent No.: US 6,262,339 B1
(45) Date of Patent: Jul. 17, 2001

(54) PROCESS FOR GENERATING MALE STERILE PLANTS

(75) Inventors: Rob Dirks, Dilsen-Stokkem (BE); Klaus Trinks, Flörsheim (DE); Bert Uijtewaal, Heythuysen (NL); Klaus Bartsch, Königstein (DE); Roger Peeters, Oss (NL); Rainer Höfgen; Hans-Dieter Pohlenz, both of Berlin (DE)

(73) Assignee: Hoechst schering AgrEvo GmbG, Berlin (DE)

( * ) Notice: Subject to any disclaimer, the term of this patent is extended or adjusted under 35 U.S.C. 154(b) by 0 days.

(21) Appl. No.: 08/556,944

(22) PCT Filed: Jun. 7, 1994

(86) PCT No.: PCT/EP94/01840

§ 371 Date: Apr. 2, 1996

§ 102(e) Date: Apr. 2, 1996

(87) PCT Pub. No.: WO94/29465

PCT Pub. Date: Dec. 22, 1994

(30) Foreign Application Priority Data

Jun. 8, 1993 (EP) .................................................. 93109226

(51) Int. Cl.$^7$ ............................. C12N 1/00; C12N 15/92; C12N 15/11; C12N 5/04
(52) U.S. Cl. ......................... 800/274; 800/271; 800/286; 800/287; 800/295
(58) Field of Search ............................. 435/172.3, 172.1; 800/205, 200, 250, 272, 274, 275, 203, 271, 286, 287, 295; 47/58, DIG. 1

(56) References Cited

U.S. PATENT DOCUMENTS 5,356,799 * 10/1994 Fabijanski et al. ................ 435/172.3
5,364,780 * 11/1994 Hershery et al. .................. 435/172.3

FOREIGN PATENT DOCUMENTS

| 92/13957 | * | 8/1992 | (EP) ................................. 435/172.3 |
| 0 513 884 | * | 11/1992 | (EP) . |
| 0 531 716 | * | 3/1993 | (EP) . |
| WO 90/08830 | * | 8/1990 | (WO) . |
| WO 91/03561 | * | 3/1991 | (WO) . |
| WO 92/04454 | * | 3/1992 | (WO) . |
| WO 92/05257 | * | 4/1992 | (WO) . |
| WO 92/11379 | * | 7/1992 | (WO) . |
| WO 93/02197 | * | 2/1993 | (WO) . |
| WO 93/18142 | * | 9/1993 | (WO) . |
| WO 93/18171 | * | 9/1993 | (WO) . |
| WO 94/09143 | * | 4/1994 | (WO) . |

OTHER PUBLICATIONS

Mo et al. Biochemical complementation of chalcone sythase mutants defines a role for flavonals in functional pollen. PNAS vol. 89 pp. 7213–7217, Aug. 1992.*
Van der Meer et al. Anther inhibition of flavonoid biosynthesis on petunia anthers result in male sterility. The plant cell. vol. 4, pp. 253–262, Mar. 1992.*
Chemical Abstracts 120(7):71368 (1994).*
Mo et al., Proc. Natl. Acad. Sci. USA.89:7213–7217 (1992).*
O'Keefe et al., Plant Physiol. 105:473–482 (1994).*
Taylor et al., Journal of Heredity 83:11–17 (1992).*
Temple et al., Mol. Gen. Genet. 236:315–325 (1993).*
Van der Meer et al., The Plant Cell 4:253–262 (1992).*
van der Krol et al. Nature vol.333 pp. 866–869, Jun. 30, 1988.*
van der Krol et al. Plant Mol. Biol. vol. 14, pp. 457–466, 1990.*

* cited by examiner

Primary Examiner—Gary Benzion
(74) Attorney, Agent, or Firm—Frommer Lawrence & Haug LLP

(57) ABSTRACT

The invention is directed to a process for the generation of male sterility in plants comprising the steps of (a) transforming a plant cell with DNA sequences that selectively inhibit the expression of essential metabolic compounds and (b) regenerating plants from said plant cells. Cells impaired in the biosynthesis of basic metabolic compounds undergo starvation and eventually die. Such pathways include amino acid biosynthesis, nucleic acid biosynthesis and other biosynthetic pathways such as citric acid cycle, pentose phosphate pathway, fatty acid metabolism, vitamin biosynthesis that will render the cell inactive due to nutrient depletion, if one or more enzymes or proteins involved in this pathway would become inactive by using inhibitory DNA constructs.

14 Claims, No Drawings

PROCESS FOR GENERATING MALE STERILE PLANTS

1. INTRODUCTION

Male sterility is a property that is highly recognized in plant breeding. Male sterility enables the combination of traits from two parental lines, with the ultimate goal to supress negative traits from either parent with the genes from the other parent, and to superimpose positive traits carried by both parents. This results in a vigour that equals or exceeds either parental line. Several natural sources, e.g. cytoplasmic sterility or systems based on nuclear male sterility are already being used for many years. In crops were natural sources of male sterility are not available or not suitable, e.g. in tomato, hand emasculation and manual hybridization is still being carried out.

Chemical companies recognize the importance of hybridization and developed chemical hybridizing agents that affect the pollenviability (and as a consequence the fertility) of the plants on which the treatment is applied (see Mabbet, 1992).

In recent years, several molecular biological approaches have led to alternative ways for introduction of male sterility in crop plants. Mariani et al. (1990) introduced a RNAse that leads to tapetum ablation and results in transgenic plants that are male sterile.

Recently, Worall et al. (1992) published a system where the premature dissolution of the microsporocyte callose wall causes male sterility in transgenic tobacco. Mol et al. (1991) found that an antisense chalcone synthase gene expressed in the flower, could result in the absence of pigmentation of the anthers and the loss of fertile pollen. Ylstra and van Tunen (1992) reported that depletion of flavonols in tapetal cells by antisense Chalcone synthase leads to a reduction in pollen viability.

Natural mutants deficient of chalcone synthase have been described already in maize (Coe et al. 1981) and produce white disfuntional pollen. Restoration to fertility could be partially obtained by pollination on wild type stigmas or by addition of micromolar quantities of kaempferol to the pollen germination medium (Mo et al. 1992). Utilization of these characteristics led to a system for male sterility and conditional male fertility when kaempferol is supplied (Van Tunen et al. 1992). The exact role of flavonoids in the flower physiology is still unknown.

The International Patent Application WO 90/08830 is directed to methods for the production of male sterile plants by the expression of either a gene encoding a protein inhibitor, or a so-called killer gene. The expression of the genes in the male flowers leads to cell death of the anthers.

The International Patent Application WO 90/08831 teaches a method for the inhibition of cell-respiration by expression of a disrupter gene. Examples for disrupter proteins are the mammalian uncoupling protein (UCP), a mutated form of the gene for the β-1 subunit of $F_1$-ATPase, and a mutated, synthetic form of the olil gene encoding subunit 9 of the $F_0$-ATPase.

The International Patent Application WO 89/10396 discloses methods for the generation of male sterile plants. The plant cells are transformed with a male-sterility DNA. Examples of such male-sterility DNA are those encoding DNAses, RNAses, proteases, or enzymes of phytohormone synthesis, such as cytokinin or antisense DNA coding for a strand of DNA complementary to a strand of DNA that is naturally transcribed in the plant cells.

EP-A-0 329 308 discloses a method to produce male-sterile plants by using anti-sense DNA. The development of functional pollen grains is blocked because of anti-sense DNA directed to genes which are specifically expressed in the microspores, preferably in the premeiotic stage.

All systems described above suffer from a serious drawback in the sense that plants are terminally male sterile because of the cell death of the tapetal cells and eventually the microspores and thus the pollengrains, or the microspores directly. Maintaining lines that carry the male sterility gene requires back crossing with a wild type isogenic line. This results in a segregation and consequent loss of 50% of this backcross population due to the fact that 50% of the lines will not carry the male sterility gene, and will be male fertile.

In order to be able to perform further breeding with those plants which have desirable properties, it is necessary to restore fertility, which is very time and cost consuming.

Auxotrophic mutants of plants are characterized by the inability to synthesise one or more enzymes involved in metabolic pathways. Such mutants have been recovered in plant cells via a variety of techniques (for a review, see Pythoud and King, 1990).

These mutants in plants are very difficult to maintain due to the stringent requirement of the metabolite that is characteristic for the mutation. Most auxotrophic cells cultured "in vitro" are unable to divide unless the required compound is supplemented in the culture medium. When such mutants are not supplemented with the required compound, the cell obviously becomes starved and eventually will die. It is however possible to reinitiate division, dependent on the time of the starvation treatment by supplementing the required metabolite (Dirks et al. 1986, Negrutiu et al. 1983 and 1985).

2. DESCRIPTION OF THE INVENTION

The invention is directed to a process for the generation of male sterility in plants comprising the steps of
(a) transforming a plant cell with DNA sequences that selectively inhibit the production of essential metabolic compounds and
(b) regenerating plants from said plant cells.

The invention is further directed to a process for the generation of conditional reversible male sterility in plants by
(a) transforming plant cells with inhibitory DNA sequences
(b) under the control of a suitable male organ specific promotor that selectively inhibits the production of
(c) essential metabolic compounds which can by supplemented and
(b) regenerating plants from said plant cells.

Cells impaired in the biosynthesis of basic metabolic compounds undergo starvation and eventually die. Such pathways include amino acid biosynthesis, nucleic acid biosynthesis and other biosynthetic pathways such as citric acid cycle, pentose phosphate pathway, fatty acid metabolism, vitamin biosynthesis that will render the cell inactive due to nutrient depletion, if one or more enzymes involved in this pathway would become inactive by a variety of means.

The term inhibitory DNA encompasses any DNA that will cause that a certain metabolic pathway is blocked, e. g. an antisense DNA. The term antisense is to be understood as a DNA sequence which is complementary to a target or substrate DNA sequence, the expression of the antisense leads to expression of an inhibitory RNA and the inhibition of the expression of the target (see also EP 140 308).

The principles of antisense RNA are described by Inouye (1988) and Izant and Weintraub (1984). Inhibitory DNA might also code for ribozymes that selectively cut and therefore inhibit target sequences (EP 321 201). But there exist also other ways to inhibit gene expression and translation.

In particular, the inhibitory DNA is transcribed in the anther cells into a RNA which selectively inhibits the expression of genes coding for enzymes or proteins which are involved in the biosynthesis of amino acids.

In particular the invention relates to plants wherein the DNA sequence is expressed under the control of a tapetum-specific promotor. Plants regenerated from plant cells with an inhibitory DNA will be unable to produce functional tapetum cells and will produce non functional pollen or no pollen at all.

The invention is also related to transgenic plants containing gene constructs comprising a male organ specific promotor operably linked to inhibitory DNA sequences. The invention also pertains to male sterile plants, parts thereof and cells as well as its reproduction material. The invention further pertains to the seeds produced by the transgenic plants and all progeny that exhibit the desirable trait herein described.

The promotor contains the DNA sequence which is necessary for the initation of transcription. Further downstream, i.e. following the promotor, is the so-called 5' non translated region which is also involved in the initiation of transcription. In most cases the promotor will be located at the 5' end of the gene, but it can also vary in its position. The coding region is followed further downstream by the so-called 3' untranslated region. This region does contain signals which cause the termination of transcription and in eucaryotic cells an additional signal that causes the polyadenylation of the transcribed RNA. Termination sequences such as 3'polyadenylation signals are also well described and used in a routine fashion (see Lloyd et al. 1986). The DNA constructs or chimeric genes may also include leader sequences and signal sequences.

The DNA sequences which regulate the expression may be derived from different sources, e.g. plant, virus or bacterial genes which are active in plants. Inducible promoters as opposed to constitutive promoters enable directed and controlled expression. Inducible promoters may be expressable depending upon the development of the cell or the type of tissue.

In a preferred embodiment the invention relates to a process wherein the male sterility is induced by expression of inhibitory DNA solely in it's male organs, especially in anther cell layers, preferably in tapetum cells.

The antisense RNA is preferentially expressed in tapetum layer in order not to disturb the physiological processes taking place in non reproductive tissues and in the female plant organs. Such anther and tapetum specific promoters or controls of expression have been published (see f.i. Seurinck et al. 1990, and Wyatt et al. 1992).

According to the instant invention said antisense genes are preferably expressed under the control of a pollenspecific promoter.

Constructs containing chimeric genes composed of a tapetum specific promotor and an antisense coding region against a well defined target at the mRNA or the HnRNA can be made according to well known procedures (see Maniatis et al. 1982).

In order to test the efficiency of a construct that directs the suppression of a particular gene by antisense/sense interactions it is possible to make constructs using a constitutive promotor sequence such as 35S (Odell et al. 1985) first. After the transformation of such constructs it is possible to quantify the effectiveness. If the sense message is prevented from translation, the transgenic cell line will show an auxotrophic requirement that corresponds exactly to the compound for which the biosynthetic pathway was interrupted.

This invention especially relates to a process that allows to control the basic metabolism of male organs by the introduction of DNA sequences that selectively inhibit the production of one or more essential compounds in the biosynthesis of amino acids.

Antisense gene expression preventing the formation of aspartokinase (Ghislain, 1992) in tapetum or microspore leads to starvation for lysine, threonine, isoleucine and methionine, and would therefore be very suitable for obtaining male sterility. The spraying with these amino acids or with aspartyl-β-phosphate or aspartate-β-semialdehyde leads to resumption of the normal metabolism.

Inhibition of the enzyme threonine deaminase leads to isoleucine deficiency.

Acetolactate synthase (ALS) inhibition (Comai et al., 1985) leads to a combined valine, isoleucine, leucine auxotrophy and non functional EPSP synthase (5-enolpyruvylshikimic acid-3-phosphate synthase) would lead to phenylalanine, tryptophan and tyrosine deprivation. Non functional dehydrodipicolinate synthase (Ghislain, 1992) leads to lysine auxotrophy.

In a further preferred embodiment the invention is directed to a process in which another enzyme involved in the biosynthesis of amino acids, the glutamine synthetase (EP-A-0 290 987) is inhibited. Ammonium ions are incorporated into glutamine by the action of this enzyme on glutamate. The glutamine synthetase plays a critical role in nitrogen metabolism. Inhibition of this enzyme leads to nitrogen starvation and consequently to male sterility.

The antisense can also be directed against introns in the heteronuclear mRNA (HnRNA) so that the splicing out of the introns would either not be possible or would lead to non sense coding information, resulting in a loss of the enzymatic function of the protein for which the corresponding RNA (mRNA or HnRNA) was targeted against by the antisense RNA.

By taking advantage of genetic engineering the gene responsible for the production of the inhibiting DNA, i. e. the antisense DNA or the ribozyme-encoding DNA, can be transferred to the genome of plant cells, which can be regenerated to whole plants.

The preparation of transformed plants comprises the following steps:

ligating the coding region of the inhibiting DNA sequence to a promotor and a terminator which is selectively active in male organ plant cells, transferring and integrating said contructed DNA sequence in the genome of a plant cell, regenerating whole plants from transformed cells.

Methods for the introduction of DNA sequences into plant cells are known in the art and therefore the DNA construct can be introduced using different techniques. The particular method which is used to introduce the DNA sequence into a plant cell is not critical.

For the stable introduction of foreign DNA constructs in plant cells and the regeneration thereof, a variety of techniques are available that can be used depending on the plant to be transformed. Techniques exist that make use of Agrobacterium tumefaciens as a vector, for example (An et al. 1986, EP 0 116 718) biolistic approaches (Klein et a. 1987)

electroporation technologies (Shillito et al. 1985), liposome mediated gene delivery (Gad et al. 1990), direct gene transfer using polyethylene glycol (Dewulf and Negrutiu, 1991) and protoplast transformation (EP 0 164 575).

No special demands are placed on the plasmids which are used. Commonly used plasmids, as e. g. pUC-derivatives, bBR322, M13 mp plasmids, EMBL plasmids can be employed.

The selection of plant cells which have been transformed is enabled by the use of a selectable marker gene which is also transferred. The expression of the marker gene confers a phenotypic trait that enables the selection. Examples for such genes are those coding for antibiotic or herbicide resistance, e.g. neomycin or phosphinothricin resistance.

In view of the great progress in plant biotechnology it is foreseeable that practically all plants can be regenerated from cultured cells or tisues, including major cereal crop species.

The range of plants in which the inhibiting DNA can be introduced will be dependent on suitable transformation protocols and methods.

Therefore, the invention is applicable to a broad range of plants used in agriculture and plant breeding. Plants which can be protected may be either monocotyledons or dicotyledons.

Examples of families that are of special interest are Solanaceae and Brassicaceae. Examples of species of commercial interest that can be protected include:
tobacco, *Nicotiana tabacum* L.
tomato, *Lycopersicon esculentum* Mill,
potato, *Solanum tuberosum* L.,
petunia, *Petunia hybrida* (Solanaceae)
Canola/Rapeseed,
*Brassica napus* L.,
cabbage, broccoli, kale etc.,
*Brassica oleracea* L.,
mustards *Brassica juncea* L.,
*Brassica nigra* L,
*Sinapis alba* L. (Brassicaceae),
sugar beet, *Beta vulgaris,* (Chenopodiaceae),
cucumber, Curcurbita sp. (Curcurbitaceae),
cotton, Gossypium sp., (Malvaceae),
sunflower, *Helianthus annuus,*
lettuce *Lactuca sativa,* (Asteraceae=Compositae),
chicore whitloff (Asteraceae),
*Daucus carota* (Apiaceae, Umbelliferae)
pea, *Pisum sativum,*
soybean, Glycine max and alfalfa,
Medicago sp. (Fabaceae=Leguminoseae),
asparagus, *Asparagus officinalis;*
gladiolus, Gladiolus sp., (Lilaceae);
corn, *Zea mays* and
rice, *Oryza sativa* (Poaceae).

In a preferred embodiment male sterility is induced in plants such as potato, tomato, wheat, cabbage, chicory whitloof and chinese cabbage.

The constructs designed for testing antisense activity of the expressed sequences are preferentially introduced into dicotyledonous plants via a binary Ti vector system in *Agrobacterium tumefaciens.* An example of a gene useful primarily as a screenable marker for identification of plant cells harbouring foreign genes is a gene that codes for an enzyme producing an chromogenic product, e. g. the beta-glucorinidase (GUS, Jefferson et al. (1987)).

The genetically created nuclear encoded tapetum specific amino acid auxotrophy in these plants leads to a conditional reversible male sterility. The plants exhibit conditionally male inferlity, but the fertility can be restored by supplying the substrate not produced due to the metabolic block, i. e. the missing amino acid(s).

This supplementation can be achieved by a variety of means. The substrates may be added (exogenous supplementation) or produced in the cells (endogenous supplementation). The internal synthesis may be dependent on the activity of another inducible promotor. In a preferred way the substrate is added or applied externally.

The invention is especially related to a process in which the fertility of the conditionally infertile plants is restored by spraying the amino acids onto the plants.

At the time of transformation, the culture medium is modified to contain the amino acid(s) or their precursors that are unable to be synthesised due to the metabolic block imposed by the expression of the transferred inhibitory DNA construct.

Supplementation of the culture medium may be carried out already at the time of the cocultivation with the bacteria. The concentration of the required metabolite in the culture medium may range from 0.001 to 10 mM, preferably from 0.01 to 1 mM, especially 0.05 mM to 0.5 mM, more preferred from 0.025 to 0.3 mM.

At the time of selection for the antibiotic resistance, the supplementation is continued. Callus or regenerated plants carrying the antibiotic resistance and supplemented with the required metabolite since the first transformation event are tested for metabolic requirements.

In this case, a piece of callus of approximately 1 to 2 mm, an internode, a leaf segment or another plant part is subcultured on callus induction and callus propagation medium (such as MS medium (Murashige and Skoog, 1962) containing 0.1 mg/l α-napthyl acetic acid and 1 mg/l Benzyladenine) or plant propagation medium (for internodes) (such as basic MS medium without growth regulators (Murashige and Skoog, 1962) without the amino acid or the amino acid precursor as mentioned above.

If the transgenic line resistant to the antibiotic effectively expresses the antisense construct targeted against the synthesis of an enzyme in a particular amino acid biosynthetic pathway, the transferred plant material stops growing (max 1 week) and dies after transfer on the minimal medium (not supplemented with the required metabolite), and shows an auxotrophic requirement corresponding to the metabolite for which the biosynthesis was impaired due to the expression of the antisense construct.

In the case that no phenotypical differences can be observed, either the antisense construct is not effective, expressed only at low levels or even absent. The distinguishment between these alternatives can be made by RNA hybridisation (northern blotting).

If protoplast transformation (direct gene transfer, see f.i. Dewulf and Negrutiu, 1991) is chosen as a method for testing the effectiveness of particular constructs, the initial culture medium is supplemented with concentrations of 0.025 to 0.08 mM of the required compound.

After microcolonies (>25 cells per colony) are being formed, the concentration is increased at levels between 0.05 and 0.3 mM in order to maintain viability and sufficient growth. The same scheme for evaluation can be followed as above: first selection for a selectable marker and subsequently testing the transformants for an auxotrophic requirement on non-supplemented medium such as described above. Such an auxotrophic requirement will also lead to cell death if the starvation period will last too long.

Those sequences that appear to be very effective for the inactivation of the expression of a particular enzyme in a metabolic pathway (f.i. amino acid biosynthesis) and as a consequence inducing an stringent supplementation requirement for growth and viability, are used for constructs driven by a tapetum specific promoter. Flowering plants expressing an effective antisense construct will be 100% male sterile while the female organs will be completely normal and fertile.

In order to obtain seeds following a self pollination, transgenic plants expressing antisense construct(s) impairing an amino acid biosynthesis are brought back to fertility by spraying the required amino acid or precursors following the metabolic block.

Spraying is performed prior to the development of reproductive tissues especially tapetal cells. Spraying is performed at least once within 5 days, preferentially within 3 days, especially preferred within 2 days. The plants are sprayed preferrentially under the leaf surface and around the flowers when these are developing. The spraying is applied until fertilization has taken place or at least to the time that functional pollen is produced. The self pollination can then be performed by hand if necessary.

The amino acid may be sprayed in any suitable formulation (see e. g. "Pesticides Formulations" (1986) by Marcel Dekker, 2nd ED., New York or "Spray Drying Handbook", (1979) by G. Goodwin, London). They are sprayed preferrentially in a water solution.

Depending on the plant the frequency of spraying as well as the concentration of applied amino acids can vary within a broad range. If the desired amino acid(s) is (are) not toxic to the plant it is no problem to spray higher concentrations than needed to restore fertility. The concentrations required for obtaining reversion of fertility may range from 0.01 to 10 mM, preferrentially from 0.3 to 5 mM, more preferrentially from 0.5 mM to 3 mM, especially preferred from 1 mM to 2 mM.

The invention also relates to a process in which the restoration of the fertility of the F1 generation is accomplished by reinitiation of normal metabolism by suppression of the expression of antisense constructs.

The safener ethyl-1-(2,4-dichlorphenyl)-5-trichloromethyl-(1H)-1,2,4-triazole-3-carboxylate (fenchlorazole-lethyl) increases the tolerance level of wheat to fenoxaprop-ethyl, when applied in mixture with this postemergence graminicide. The safener treatment accelerates the rate of hydrolysis of the herbicide by induction of an isoenzyme gene of the glutathion-S-transferase family, which efficiently inactivates the herbicide by conjugation with glutathione. The enzyme is not present in untreated plants and is strictly dependent on spraying with the compound. This effect is apparent only a few hours after treatment of the plants. The induced state lasts for several days after one application of the chemical safener. It can be extended for a longer period by application of the safener as seed treatment or by several rounds of spraying.

Similar observations have been made for certain mixed function oxidases, which can be induced by chemical safeners for efficient inactivation of sulfonyl urea herbicides by hydroxylation.

In order to make use of these chemical inducible promoters to restore conditional male fertility in plants which were rendered male sterile by specific expression of an antisense construct in tapetum cells these promoters will be used to drive the controlled expression of a sense copy of the inactivated gene which is not related to the antisense construct.

This is achieved with a gene from an unrelated species with similar enzymatic activity or with another copy of the endogenous gene. If the antisense construct is driven against intron sequences of the target gene, an inducible cDNA copy from the same gene is sufficient for induction of fertility.

Transformed plants harbouring this type of construct are restored to male fertility by spraying the plants with the chemical safener in concentrations around 100 gAl/ha.

The effect attenuates within a few days. But the spraying can be repeated for several times if necessary.

The time course of the conditional male fertility is controlled in an easy way by choosing the time and the number of sprayings in the field. Conditional male fertility is important for maintaining the male sterile culture. A DNA sequence exhibiting inducible enzymatic activity from wheat was isolated.

For crops such as chicory witloof or different kinds of cabbages where the product to be harvested are the leaves, the F1 hybrid is to be made by crossing a male sterile motherplant obtained by the procedure as described above, with another selected male parent. This leads to a male sterile F1 hybrid; this is for such crops however not relevant because of the use of only the leaves. For crops that require self pollination for fruit setting such as tomato, fertility in the F1 hybrid has to be restored. This can be done by crossing the F1 hybrid which has to be restored.

The male sterile line can be crossed with a transgenic line that encodes a functional gene that when transcription takes place will result in a functional protein, restoring the deficiency introduced by the antisense construct.

This means that the restorer, and parental line must produce a functional mRNA that will not be recognized by the antisense RNA from the female parent. In order to achieve that, an antisense RNA against the introns is introduced in the line that has to be made male sterile and by introducing a cDNA copy of the gene in the paternal line. In the F1 hybrid, the mRNA encoded by the cDNA will not be recognized by the antisense RNA and normal metabolic activities will be restored resulting in a fertile F1 hybrid plant.

An analogous procedure is followed if a structural gene having a significantly different sequence (e.g. from a microorganism such as yeast, or another plant species) would come to expression, also not being recognized by the antisense RNA.

The process according to the instant application does not have the negative side effects (50% loss by maintaining the maternal male sterile line) and does not require chemically complex molecules for conditional male fertility, such as kaempferol which might be toxic for humans and therefore undesirable to work with.

3. METHODS AND EXAMPLES

In the following ways to carry out the invention are described. The invention is described in detail hereinafter, especially in its preferred embodiment by way of examples for non-limitive illustration purposes.

Methods of culturing bacteria, preparing DNA, and manipulating DNA were as described by Maniatis et al. (1982) unless otherwise stated. Restriction enzymes and other enzymes used in DNA manipulations were obtained from Boehringer Mannheim (Mannheim, Germany), Bethesda Research Laboratory, (Gaithersburg, USA) or Sigma (Deisenhofen, Germany) and were used according to the manufacturers's specifications.

3.1 General Technical procedures.

3.1.1 Testing the specificity of functional anther specific promoters.

The *Arabidopsis thaliana* A9 gene promoter and the Antirhinum promoter TAP1 were tested for their specific expression both in Arabidopsis and N. tabacum by means of the β-glucuronidase system basically as described by Martin et al., 1992 and Scott, 1993.

3.1.2 Nucleic acid manipulations.

RNA and DNA preparations, blotting procedures, hybridization with random primed labeled probes (Boehringer Kit) and standard recombinant DNA techniques were performed as described by Sambrook et al., 1989 and Jackson et al., 1993.

Usually 30 µg total RNA or 50 µg DNA digested with a suitable restriction enzyme were applied to the gels. Sequencing was done using a Pharmacia T7 sequencing kit and sequence analysis was performed on a VAX III using the University of Wisconsin GCTG-programs.

3.1.3 Assay of ALS activity.

ALS activity was determined essentially as described by Miflin (1971). Protein was extracted from about 100 mg plant material followed by a fractionated ammoniumsulfate precipitation (25–70%) using 100–1000 µg of the precipitate for further assays with 40 mM sodium pyruvate as substrate and 0.32 mM thiaminpyrophosphate as coenzyme in presence of 0.5 mM $MnSO_4$ in 20 mM sodium-phosphate buffer, pH 7.5: incubation was for 1 h at 30° C., the enzyme reaction was stopped with 5 mM $ZnSO_4$, the supernatant acidified with HCl to decarboxylate the reaction product acetolactate to acetoin. After addition of 1.7% alphanaphtol and 0.17% creatin and 1 h incubation at room temperature the absorbance of the samples was detected at 530 nm.

3.1.4 Transformation procedures.

Arabidopsis thaliana (L.) Heynh. ecotype C24.

A protocol was used, based on the publication of Valvekens et al., 1988, and modified according to Vergunst et al. as described below.

All media are used as described by Valvekens te al., 1988, unless otherwise stated.

3.1.5 Seed sterilization and root culture.

Weigh about 3 mg seeds in an eppendorf tube (250 ml flask).
Sterilize the seed for about 60 sec in 70% ethanol, 10 minutes in 1% hypochlorite solution containing Tween 20 (add a few drops to 20 ml).
Rinse the seeds 3 to 4 times in sterile water.
Add seeds to 50 ml liquid B5 medium (Gamborg et al., 1968) containing 20 g/l glucose as a source of carbon) in a 250 ml flask.
Put flasks on a shaker (100 rpm) in growth room (21° C., 16 hrs light/8 hrs dark, 2000 lux).
Use roots of 10 day old cultures (differing light conditions might need older or younger cultures) for transformation.

3.1.6 Transformation.

In order to increase the gas exchange urgopore tape was used as described by Valvekens et al., 1988). All plates were dried for about 45 minutes in airflow cabinet (condensation can cause growth of Agrobacteria and yield vitrified shoots). Care was taken that the agar was not too soft; this would make plating of the root explants more difficult. The following steps were performed:
Separate roots from hypocotyls, cotyledons and leaves.
Place the roots in callus induction medium (CIM) containing plates. Be careful that all roots are in good contact with the agar medium. Usually use one plate per flask.
Incubate the roots for 3 days in a growth room at 25° C. at 2000 lux.
Inoculate Agrobacterium strain(s) in 10 ml LC containing antibiotics from a freshLC-plate and grow culture overnight at 29° C. in a shaking waterbath (the culture can also be inoculated on FR and kept at 4° C. until SU, e. g. LBA 115 (0 MOG101)). Measure the $OD_{600}$ of the overnight Agrobacterium culture, resuspend and dilute it to obtain a final $OD_{600}$ of 0.1.
Transfer the roots to a sieve that is placed in 40 ml liquid B5 medium in a petridish.
Add bacteria to petridish containing the sieve with the roots. Shake during 2 minutes.
Take the roots and place them in a petridish. Cut the roots in pieces of 3 to 5 mm (named explants).
Dry the excess liquid with sterile filterpaper.
Plate the root explants on CIM medium, again make sure the explants are in close contact with the medium.
Incubate the roots for 2 days in a growth room (25° C., 2000 lux). After this period, collect the root explants (bacteria will have overgrown the explants) and place in a sieve in liquid B5.
Wash roots carefully by shaking sieve. Repeat the washing step in fresh B5.
Blot root explants on dry sterile filterpaper. (root explants should be dry, but not dried out).
Place the explants to SIM containing the selectable marker (f.i. 50 mg/l kanamycin) and antibiotics to kill remaining Agrobacteria (f.i. 750 mg/l vancomycin or 200 mg/l carbenicillin in combination with 500 mg/l vancomycin).
The utilization of cefotaxim in the transformation of Arabidopsis is possible but known to interfere with the ability for regeneration.
Transfer the explants to fresh shoot inducing medium (SIM) every 7 to 10 days. After 3 weeks the concentration of carbinicillin and vancomycin can be decreased. When calli can be picked up individually (usually after 2 to 3 weeks) transfer approximately 100 calli per SIM plate.
Transfer little shoots without any callus to plates with MA (Masson and Paszkowski 1992) containing 1 mg/l indol butyric acid (and no selection) (=rooting medium) for 1 week. Put the plates at 21° C. at 3000 lux.

|     |                          | per liter |
| --- | ------------------------ | --------- |
| MA: | MS macro 1/2 strength (10x) | 50 ml  |
|     | FeNaEDTA                 | 10 ml     |
|     | B5 microelements (100x)  | 1 ml      |
|     | 1% sucrose               | 10 g      |
|     | 0.1% MES                 | 1 g       |
|     | 0.8% Agar                | 1 g       |
|     | pH 5.8/sterilized by autoclaving |   |

Growth conditions: 16 hrs light, 8 hrs dark, 21/25° C. with different light intensities (see text).

* Transfer shoots to larger jars if necessary.

3.1.8 Plant transformation of Nicotiana tabacum (Samsun NN, SR1 and Solanum tuberosum (cultivar Desirée).

Tissue culture and transformation of leaf discs was essentially performed as described by Rocha-Sosa et al., 1989. Potato leaf discs of the commercial cultivar Desirée and the tobacco cultivars SR1 and Samsun NN were used as explants. Agrobacterial growth after the cocultivation was inhibited by the addition of cefotaxim. Selection of transformants was carried out by the addition of kanamycin in the culture medium.

Transformation with Agrobacteria that constitutively express antisense RNA against acetolactate synthase: in these experiments 500 mg/l casamino acids or a combination of 0.1 mM L-valine, L-leucine and L-isoleucine were supplemented during all tissue culture procedures.

In order to test the principle of the mechanism proposed to create an auxotrophic requirement in anther tissues leading to conditional (but reversible) non functional pollen, acetolactate synthase (ALS) was studied as a model target gene. The sequence of the ALS of *Arabodopsis thaliana* has been published by Sathasivan et al (1 990).

3.2 Construction of an ALS antisense gene and vector systems

The potato ALS gene was cloned by a nested PCR approach into the PCR 1000 vector system because the first set of primers only yielded faint and ambigious bands.

Nested PCR primers are ones that are internal to the first primer pair. The larger fragment produced by the first round of PCR is used as the template for the second PCR. Nested PCR can also be performed with one of the first primer pair and a single nested primer. The sensitivity and specificity of both DNA and RNA can be significantly increased by using this method.

The primers were homologous to the sequence of the tobacco SurB gene (database accession number X 07645, Lee et al., 1988) and the first pair comprised position 415–444 respectively 2376–2409 and the second more inward pair of primers 445–477 respectively, 2341–2375. The 5'oligo was provided with an EcoRI site and the 3'oligo with an additionally BamHI site for cloning purposes. An Asp 718/NotI fragment of the ALS gene was cut from this vector, blunted and ligated into the SmaI of pUC 19.

A KpnI/SalI fragment with suitable orientation was removed from pUC-ALS and cloned into the expression cassette of a plant binary vector, Bin AR (Höfgen and Willmitzer, 1990), resulting in a potato ALS gene in antisense orientation with respect to the CaMV 35S promoter of the expression cassette; plant termination sequences were provided by an octopine synthase 3'end. The plasmid was designated pH29.

3.3 Isolation of a 355 bp anther/tapetum specific promoter

A 355 bp anther/tapetum specific promoter fragment from the A9 gene of *Arabidopsis thaliana* (Paul et al., 1992) was generated by the construction of two primers, one at position 1084–1106 containing a HindIII site at position 1089–1094 and the other one at position 1425–1448 containing a XbaI site at position 1138–1143, respectively, using the polymerase chain reaction.

3.4 Construction of an anther/tapetum specific promoter-GUS fusion plasmid

The 355 bp promoter fragment was cloned into the HindIII-XbaI cut pBI/101 vector (Jefferson et al., 1987) forming pNun3.

3.5 Construction of anther/tapetum targeted promoter-antisense gene fusion plasmids The potato ALS gene as described above was recloned from pH29 into BamHi/SacI cut pNun3 forming pNun5 by using a primer pair with unique restriction sites. The first primer at position 445–478 contained a SacI site at its 5'-end.

The second primer at position 2340–2375 contained a BamHI site at its 5'-end. Another fusion plasmid of an antisense potato ALS gene behind an anther/tapetum specific promoter was created by ligation of a BamHI cut pVDH187 with the BamHI cut potato ALS gene out of pH29 forming pVDH92 after control of proper orientation. pVDH187 was originally derived from pBIN19 (Bevan, 1984) in which the TapI promoter of Antirhinum (Nacken et al., 1991) was ligated after EcoRI/BamHI digestion.

This promoter was followed by a BamHI/HindIII ligated polyadenylation signal from the nopaline synthase gene of the agrobacterium Ti plasmid. In the opposite direction, a GUS-intron gene (Vancanneyt et al., 1990) in between the CaMV 35S promoter and polyadenylation signal was ligated in this plasmid after HindIII digestion.

Further an antisense-tapetum promoter construct was created with an Arabidopsis ALS gene (database accession number X51514, Sathasvisan et al., 1990). After DraI/BglII digestion, BglII linkers were ligated to the Arabidopsis ALS gene fragment. The BglII cut fragment was inserted into BamHI cut pVDH187 forming pVDH190 when antisense orientation was checked.

3.6 Transformation experiments

In a first set of experiments, tobacco and potato explants were transformed with an ALS gene placed in reverse orientation, under the control of a constitutive promoter.

An antisense ALS gene (pH29) was constructed under control of the heterologous constitutive 35S CaMV promoter and transferred to *Agrobacterium tumefaciens* pGV2260. This Agrobacterium strain (H29) was applied for a standard leaf disc transformation procedure of potato plants. Rooted plantlets were replicated and one copy of each plant was transferred to MS medium (Murashige and Skoog, 1962) without casamino acid complementation, to screen for plants unable to grow without exogenous supply of amino acids.

Two potato plants (P.H. 29-2, and -41) exhibited clear growth retardation under these conditions but recovered when put back to complementing medium. About 40 individual replicas of the potato plants were put to soil and grown under greenhouse conditions for a phenotypic evaluation.

Three potato plants (P.H. 29-41) developed phenotypical symptoms, two plants only initially after potting but recovering later. Plant P.H: 29-41 exhibited constantly severe phenotypical symptoms: strong growth retardation and stunting, leaf chlorosis, bushy growth and alteration of the leaf morphology to crumpled, small simple leaves without formation of the potato typical compound leaves. Several siblings of P.H. 29-41 usually even died soon after transfer from tissue culture to soil.

In a second set of experiments Arabidopsis and tobacco explants were transformed with either GUS or antisense ALS gene constructs under the control of anther/tapetum specific promoters. pNun3 and pNun5 were transferred to the Agrobacterium tumefaciens strain EHA101 (pAtHV RKGM, Hood et al., 1986), whereas the other plasmids pVDH190 and pVDH192 were transferred to the Agrobacterium tumefaciens strain LBA4404 (pToK47, Jin et al., 1987). The transformed strains were called Nun3, Nun5, VDH190 and VDH192, respectively. (See further 3.9 Male sterility and reversion to fertility).

3.7 Molecular analysis of ALS antisense plants.

Genomic southern blots were performed to correlate phenotypical symptoms and the integration of ALS antisense genes.

Additional bands hybridizing to an ALS probe proved that the plants investigated are transgenic ALS antisense plants. Northern blot analysis of total RNA from leaf tissues of Desiree control plants showed a hybridisation signal of about 2kbp, the expected size for an ALS mRNA signal. The steady state mRNA of ALS were slightly higher for older than for younger leaf tissues. In northern blot analysis the ALS antisense plants P.H 29-2 and P.H 29-41 both showed a reduction of ALS mRNA level when compared to the controls.

Steady state ALS mRNA content of plant P.H 29-41 was even lower than those of plant P.H 29-2, which positively correlates to the severity of the phenotypical effects observed. Both ALS antisense plants exhibited reduced ALS RNA amounts but not complete extinction of the enzymatic activity. Hybridisation to other genes coding for enzymes within the same biosynthetic pathway, i.e. threonine deaminase (Hildmann et al., 1992) did not show any differences in expression between antisense and control plants. Apparently, there are no major changes in the expression of other amino acid biosynthetic genes to compensate for the reduced level of ALS mRNA and enzyme amounts.

3.8 ALS antisense plants show reduced level of enzymatic activity.

Antisense inhibition of ALS led to a reduced availability of the corresponding mRNA for translation which should result in a reduced content of this enzyme in plant tissues. ALS assays were performed with tissues of control plants of different developemental stages: very young tissue near to the vegetative bud, fully developed and expanded leaves and old but still green leaves at the stem base (Table 1).

TABLE 1

ALS activity in different tissues of control plants and of transgenic ALS antisense plants a) Determination of ALS activity in different tissues of potato control plants

| | number of samples | relative enzyme activity [delta E/mg fw] | |
| --- | --- | --- | --- |
| shoot tip and young leaves | 15 | 1.03 +/− 0.05 | 100% |
| middle leaf | 16 | 0.2 +/− 0.03 | 19.4% |
| old leaf | 21 | 0.18 +/− 0.02 | 17.5% | b) Comparison of the ALS activities of control plants and ALS antisense plants. Samples were taken from young tissues

| Sample | Number of samples | relative enzyme activity [delta E/mg fw] | [%] |
| --- | --- | --- | --- |
| Désirée control plants | 20 | 1.6 +/− 0.24 | 100 |
| 29-2 | 10 | 0.53 +/− 0.11 | 33.1 |
| 29-41 | 20 | 0.23 +/− 0.06 | 14.4 |

Tissue samples were taken from plants transferred from tissue cultures to soil and grown under similar green house conditions for the same time (fw=fresh weight).

The highest enzyme activity was measured in young leaves, whereas all other material showed ALS activities reduced by a factor of about 5. The variability of ALS activity between different control plants was low (15% standard deviation). All further ALS assays were carried out using young developing tissues.

The ALS activity of P.H. 29-2 was reduced to 33% of wild type activity and the phenotypically severely affected plant P.H 29-41 showed only 15% of wildtype activity (Table 1). Thus, ALS antisense plants showed a clear correlation of phenotype and the reduction of ALS activity when compared to control plants. 15 % remaining enzyme activity of ALS is just sufficient to sustain growth of the transgenic plant P.H 29-41. The reduction in enzymatic activity correlates to the results obtained in northern blot analysis.

It was possible to achieve a reduction in the steady state levels of ALS mRNA in transgenic plants as primary effect of ALS antisense gene expression. The ALS signal in northern blots of transgenic plants was reduced only partially, which corresponds to the fact that ALS enzyme activity is only moderately reduced in the se plants but sufficient to generate phenotypical effects.

It has been shown that amino acid biosynthetic pathways are highly regulated on the enzyme level (Bryan, 1990), however, it could be possible that additionally transcriptional regulation of the appropriate genes might occur. Therefore, ALS antisense plants were scored for transcriptional regulation of some other key regulatory enzymes with in the affected pathway (see above). We found no alteration when compared to RNA of the control plants.

3.8 Experimental evidence for male sterility using antisense ALS driven by anther specific promoters To assess the organ specificity of promoter action, the β-glucuronidase gene was fused to the anther specific promoters and Gus assays were performed basically as described by Martin et al., 1992 and Scott, 1993. In Arabidopsis as well as in tobacco, the expression of the antisense was clearly confined solely to anther tissue and the expression specificity and timing were comparable to the patterns as described by Scott, 1993.

3.9 Male Sterility and reversion to fertility

N. tabacum and Arabidopsis thaliana were transformed with gene constructs expressing an antisense ALS gene under the control of anther specific promoters A9 and Tap1 respectively. Of several hundred independent transformants, with the bacterial strains Nun 3, 5 and VDH 19 0 and 192 respectively, selected by means of kanamycin resistance and by the confirmation of the transgenic nature of the transformants by means of a β-glucuronidase assay, several sterile plants or plants with reduced fertility and without seed set were recovered. Molecular analysis is currently carried out to confirm the relation between the reduction of ALS in the anther tissue and the observed decrease of fertility.

For the Arabidopsis genotype (C-24) 340 individual transformants were obtained. 36 out of these 340 putative sterile plants produced pollen that was not stainable and in several cases the morphology of the pollen was clearly abnormal (broken pollen).

Complementation and testing of conditional male fertility was confirmed by spraying of the required metabolites: L-leucine, L-valine and L-Isoleucine as described in the specification.

The above given data show that mutants deficient for the biosynthesis of several amino acids are unable to grow in the soil but could be rescued by the spraying of amino acids and that these conditional unfertile plants carry fertile pollen, whereas no treatment leads to death of the auxotrophic plant with unfertile pollen.

4. REFERENCES

An G., Watson B. and Chiang C. (1986) Transformation of Tobacco, Tomato, Potato and Arabidopsis thaliana Using a Binary Ti Vector System. Plant Physiol. 81, 301–305.

Bevan M (1984) Nuc Acid Res 12, 8711–8721.

Botterman J. and Leemans J. (1988) Engineering herbicide resistance in plant. Trends in Genetics, 8, 219–222.

Bryan J K, (1980) Encycl Plant Physiol New Ser 14A, 5–64

Gad A. E., Rosenberg N. and Altman A. (1990) Liposome-mediated gene delivery into plant cells. Physiologica Plantarum 79, 177–183.

Coe E. H., McCormick S. M. and Modena S. A. (1981) J. Hered 72, 318–320.

Comai L. and Stalker D. (1986) Mechanisms of action of herbicides and their molecular manipulation. Oxford Surveys of Plant Molecular & Cell Biology, vol. 3. pp 166–195.

Comai L, Facciotti D, Hiatt W, Thompson G, Rose R and Stalker D. (1985). Expression in plants of a mutant aroA gene from Salmonella tyhimurium confers tolerance to glyphosate. Nature 317, 741–745.

Dewulf J. and Negrutiu I. (1991) Direct gene transfer. Direct gene transfer into protoplasts: The chemical approach. In: A laboratory guide for cellular and molecular plant biology. Eds. I. Negrutiu and G. Gharti-Chhetri. Birkhäuser Verlag. Basel.

Dirks R., Negrutiu I., Jacobs M. and Sidorov V. (1986) Isolation of auxotrophic mutants based on reconstruction experiments with Nicotiana plumabaginifolia protoplasts. In: Genetic manipulation in plant breeding. eds W. Horn, C. J. Jensen, W. Odenbach, O. Schieder. Walter de Gruyter. Berlin. New York. pp 599–600.

Gamborg O L, Miller R A, Ojima K (1968) Exp Cell Res 50, 151–158.

Ghislain M. (1992). Molecular analysis of two key enzymes of the plant aspartate family amino acid pathway: aspartate kinase and dihydropicilonate synthase. Vrije Universiteit Brüssel. Vol. III, Proefschrift.

Gray J, Picton S, Shabbeer J, Schuch W and Grierson D (1992). Molecular biology of fruit ripening and its manipulation with antisense genes. Plant Molecular biology 19: 69–89.

Hildmann T, Ebneth M, Pena-Cortes H, Sanchez-Serrano J, Willmitzer L, Prat S (1992) Plant Cell 4, 1157–1170.

Hood E E, Helmer G L, Fraley R T, Chiltron M D (1986) J Bact 168, 1291–1301.

Inouye M. (1988) Antisense RNA: its function and applications in gene regulation: a review. Gene 72, 25–34.

Izant J. G. and Weintraub H. (1984) Inhibition of thymidine kinase gene expression by antisense RNA: a molecular approach to genetic analysis. Cell 36, 1007–1015.

Jackson S, Sonnewald U, Willmitzer L (1993) Mol Gen Genet 236, 309–314.

Jefferson R A, Kavanaugh T A, Bevan M W (1987) EMBO J 6, 3901–3907.

Jin S, Komari T, Gordon MP, Nester EW (1987) J Bact 169, 4417–4425.

Kamin H. and Stein Privalle L. (1987) Nitrite reductase. In: Inorganic Nitrogen Metabolism. Eds. W. R. Ullrich, P. J. Aparicio, P. J. Syrett and F. Castillo. Springer-Verlag Berlin. pp 113–118.

Klein T. M., Wolf E. D., Wu R. and Sanford J. (1987) Highvelocity microprojectiles for delivering nucleic acids into living cells. Nature 327, 70–73.

Köcher H. (1983) Influence of the light factor on physiological effects of the herbicide Hoe 39866. Aspects of Applied Biology 4, 227234.

Lloyd A., Barnason A., Rogers S., Byrne M., Frayley R. and Horsch R. (1986) Transformation of Arabidopsis thaliana with Agrobacterium tumefaciens. Science 234, 464–466.

Mabbett T. H. (1990) Chemical Hybridsing Agent cuts costs. Prophyta Oct. 2, 1992, pp 30–31.

Maniatis T., Fritsch E. F., and Sambrook J. (1982) Molecular Cloning: A Laboratory Manual (Cold Spring Harbor, NY: Cold Spring Harbor Laboratory).

Mariani C., De Beuckeleer M., Truettner J., Leemans J., and Goldberg R. B. (1990). Induction of male sterility in plants by a chimeric ribonuclease gene. Nature vol 347 nr. 6295, pp 737–741.

Martin T, Wöhner R, Hummel S, Willmitzer L, Frommer W (1992) In: GUS Protocols: Using the GUS gene as a Reporter of Gene Expression. pp 23–43. Eds. Sean R. Gallagher. ACADEMIC PRESS, INC. San Diego, Calif. ISBN 0-12-274010-6.

Mason and Paszkowski (1992). The Plant Journal 2, pp 829–833.

Miflin B (1971) Arch Biochem Biophys 146, 542–550.

Mol J., van der Meer I., Stuitje T., and van Tunen A. (1991). Inhibition of flavonoid biosynthesis in anthers of petunia hybrida by an antisense approach: a novel way to engineer nuclear male sterility. In: Program and Abstracts of The International Society for Plant Molecular Biology. Third International Congress. Molecular Biology of Plant Growth and Development. Tucson Arizona October 6–11, abstract nr 98.

Mo Y., Nagel C. and Taylor L. P. (1992) Biochemical complementation of chalcone synthase mutants defines a role for flavonols in fuctional pollen.

Murashige T. and Skoog F. (1962). A revised medium for rapid growth and bio assays with tobacco tissue cultures. Physiol. Plant. 15, 473–497.

Nacken W K F, Huijser P, Beltran J P, Saedler H, Sommer H (1991) Mol Gen Genet 229, 129–136.

Negrutiu I, De Brouwer D, Dirks R, Jacobs M (1985) Mol Gen Genet 199, 330–337.

Negrutiu I., De Brouwer D., Dirks R. and Jacobs M. (1985). Amino acid auxotrophs from protoplast cultures of Nicotiana plumbaginifolia, Viviani. 1. BUdR enrichment selection, plant regeneration, and general characterization. Mol Gen Genet 199, 330–337.

Negrutiu I., Dirks R. and Jacobs M. (1983) Regeneration of fully nitrate reductase-deficient mutants from protoplast culture of Nicotiana plumbaginifolia (Viviani) Theor Appl Genet 66, 341–347.

Odell J. T., Nagy F., and Chua N. -H. (1985) Identification of DNA sequences required for activity of the cauliflower virus 35S promotor. Nature 313, 810–812.

Paul W, Hodge R, Smartt S, Draper J, Scott R (1992) Plant Mol Biol 19, 611–622.

Phythoud F. and King P. J. (1990). Auxotrophic, Temperature-Sensitive and Hormone Mutants Isolated in vitro. In Plant Cell Line Selection. Procedures and Applications. Eds P. J. Dix. VCH publishers, Inc., New York, N.Y. (USA).

Rocha-Sosa M, Sonnewald U, Frommer W, Stratman M, Schell J, Willmitzer L (1989) EMBO J 8, 23–29.

Rocha-Sosa M (1990) Mol Gen Genet 220, 245–250.

Sambrook J, Fritsch EF, Maniatis T (1989) Molecular Cloning. Cold Spring Harbor Laboratory Pres. ISBN 0-87969-309-6.

Sathasivan K, Haughn G, Murai N (1990) Nucl Acids Res 18, 2188.

Scott R (1993) In: The molecular biology of flowering. pp 141–185. Eds. Br. Jordan. CAB international ISBN 0 85198 723 0.

Seurinck J., Truettner J. and Goldberg R. (1990) The nucleotide sequence of and anther-specific gene. Nucleic Acids Research, 18, 3403.

Shilito R. D., Saul M. W., Paszkowski J., Müller M. and Potrykus I. (1985) High efficiency direct gene transfer to plants. Bio/technology 3, 1099–1103.

Valvekens D, Van Montagu M, Van Lijsebettens M (1988) Proc Natl Acad Sci 85, 5536–5540.

Vancanneyt G, Schmidt R, O'Conner-Sanchez A, Willmitzer L, Rocha-Sosa M (1990) Mol Gen Genet 220, 245–250.

Van Tunen A., Van Der Meer I., and Mol J. (1992) Male-sterile plants, method for obtaining male-sterile plants and recombinant DNA for use therein. International plant application number PCT/NL92/00075.

Vaucheret H., Kronenberger J., Lepingle A., Vilaine F., Boutin J -P. and Caboche M. (1992) Inhibition of tobacco nitrite reductase activity by expression of antisense RNA. The Plant Journal 2, 559–569.

Vergunst A et al. (lab of prof. Dr. P. Hooykaas: Clusius Laboratory, Institute of Molecular Plant Sciences, Wassenaarseweg 64, 2333 AL Leiden. The Netherlands (manuscript in preparation).

Wallace W. (1987) Regulation of Nitrate Utilization in Higher Plants. In: Inorganic Nitrogen Metabolism. Eds. W. R. Ullrich, P. J. Aparicio, P. J. Syrett and F Castillo. Springer-Verlag Berlin. pp 223–230.

Worall D., Hird D. L., Hodge R., Wayatt P., Draper J. and Scott R. (1992). Premature Dissolution of the Mircrosporcyte Callose Wall Causes Male Sterility in Transgenic Tobacco. The Plant Cell 4, 759–771.

Wyatt P., Hodge R., Smart S., Draper J. and Scott R. (1992) The isolation and characterization of the tapetum-specific Arabidopsis thaliana A9 gene. Plant Molecular Biology 19, 611–622.

Ylstra B. and van Tunen A. J. (1992) F1 hybrid seed production and flavonoids. Prophyta, June, pp 56–58.

What is claimed is:

1. A process for the generation of plants that are conditionally reversible male sterile, said process comprising:
    a) transforming plant cells with a DNA sequence under the control of a male organ specific promoter, wherein expression of said DNA sequence selectively inhibits the production of one or more essential compounds in the biosynthesis of amino acids and whereby said metabolic starvation is reversible by the application of said amino acids;
    b) regenerating plants from said plant cells; and
    c) selecting said conditionally reversible male-sterile plants from said regenerated plants.

2. The process according to claim 1, wherein said DNA sequence encodes an antisense RNA which selectively inhibits the production of one or more essential compounds in the biosynthesis of amino acids.

3. The process according to claim 1, wherein expression of said DNA sequence selectively inhibits acetolactate synthase and whereby said metabolic starvation is reversible by the application of L-leucine, L-valine and L-isoleucine.

4. The process according to claim 1, wherein said DNA sequence is under the control of an anther-specific promoter.

5. The process according to claim 1, wherein said DNA sequence is under the control of a tapetum-specific promoter.

6. The process according to claim 1, wherein said DNA sequence is under the control of a pollen-specific promoter.

7. Plant cells containing gene constructs comprising a male organ specific promoter operably linked to a DNA sequence, whereby expression of said DNA sequence selectively inhibits the production of one or more essential compounds in the biosynthesis of amino acids in said male organ causing metabolic starvation in said male organ.

8. The plant cells of claim 7, whereby said metabolic starvation is reversible by the application of said amino acids whose production is inhibited by expression of said DNA sequences.

9. A male sterile plant, cells or reproduction material thereof, said plant obtainable by a process according to claim 1.

10. A process for the restoration of male-fertility in a conditionally reversible male sterile plant containing a DNA sequence under the control of a male organ specific promoter, wherein expression of said DNA sequence selectively inhibits the production of one or more essential compounds in the biosynthesis of amino acids in said male organ causing metabolic starvation in said male organ, said process comprising: supplying said amino acid whose production is inhibited by said DNA sequence to the plant to restore the male fertility.

11. The process according to claim 10, wherein said DNA sequence encodes an antisense RNA which selectively inhibits the production of one or more essential compounds in the biosynthesis of amino acids in said male organ causing metabolic starvation in said male organ.

12. The process according to claim 11, wherein expression of said DNA sequence selectively inhibits acetolactate synthase and whereby said metabolic starvation is restored by supplying L-leucine, L-valine and L-isoleucine.

13. The process of claim 10, wherein said amino acid is supplied by externally applying it to said conditionally reversible male sterile plant.

14. The process of claim 10, wherein said amino acid is sprayed onto said plant.

* * * * *